United States Patent [19]

Miura et al.

[11] Patent Number: 5,447,721
[45] Date of Patent: Sep. 5, 1995

[54] SUPEROXIDE ELIMINATING AGENT

[75] Inventors: Yasutaka Miura, Takatsuki; Masako Higuchi, Neyagawa; Yasuhiro Knoshita, Neyagawa; Yoshikazu Yamamoto, Neyagawa; Hajime Ohigashi, Kyoto; Koichi Koshimizu, Nara, all of Japan

[73] Assignee: Nippon Paint Co., Ltd., Osaka, Japan

[21] Appl. No.: 297,716

[22] Filed: Aug. 30, 1994

Related U.S. Application Data

[63] Continuation of Ser. No. 25,761, Mar. 3, 1993, abandoned.

[30] Foreign Application Priority Data

Mar. 7, 1992 [JP] Japan ................................. 4-084690

[51] Int. Cl.$^6$ ............................................. A61K 35/78
[52] U.S. Cl. .............................. 424/195.1; 424/94.4
[58] Field of Search ....................................... 424/195.1

[56] References Cited

U.S. PATENT DOCUMENTS 4,150,123  4/1979  Szturma ........................... 424/195.1

*Primary Examiner*—John W. Rollins
*Attorney, Agent, or Firm*—Townsend & Banta

[57] ABSTRACT

Disclosed is a superoxide eliminating agent comprising a component extracted from natural lichens or lichen cultures, and a process for producing the same. Cosmetics containing the superoxide eliminating agent are also disclosed.

19 Claims, No Drawings

SUPEROXIDE ELIMINATING AGENT

CROSS REFERENCE TO RELATED APPLICATION

This is a File Wrapper Continuation Application of U.S. Patent Application Ser. No. 08/025,761 filed Mar. 3, 1993, now abandoned.

FIELD OF THE INVENTION

The present invention relates to cosmetics for preventing oxygen disorder arisen on a skin, a superoxide eliminating agent which can be employed in the field of drugs (e.g. therapeutic agent for ischemic cardiac disease, antiphlogistic, etc.) and a process for producing the same.

BACKGROUND OF THE INVENTION

Lichens are consortiums consisting of some kinds of fungi and algae and belong to a group of plants which occupy a botanically specific position. Metabolites of these lichens, that is, lichen components are quite different from components of other various higher or lower plants and they belong to a botanically specific class. They are definitely classified by Asahina et al. [see Asahina and Shibata, "Chemistry of Lichen Components", published by Kawade Shobo, 1948].

It has been considered that a physiological significance of lichen components exists in defense against attack of microorganisms or insect plague because lichens grow slowly, or it exists in defense against ultraviolet ray because they grow in the sunshine, different from other fungi. Therefore, lichen components have hitherto been used for applications which came out of these functions. Examples thereof include dyes, antibiotics, falvors and the like. However, in fact, little study has been made on a pharmacological effect of these lichen components.

Lichens grow slowly and, further, their growth is liable to be restricted by natural environments (e.g. season, climate, temperature, latitude, etc.) as well as artificial environments (e.g. sulphur dioxide gas concentration, smoke concentration, etc.). Therefore, it is extremely difficult to culture lichens, which results in no success. Further, as is often the case in lichens, there the two are similar in form, but totally different in component. Therefore, selection of raw materials requires great skill and it is difficult to collect from nature. In order to obtain a method for producing lichen components, a study on cell culture has recently been made. Since lichens grow rapidly by cell culture in comparison with natural culture which needs a growth period of years or months. Therefore, it is possible to produce a subjective component in a short period of time. Further, different from a natural culture, there are advantages that is is influenced by the weather and need not a lot of persons on collection and, further, it is possible to conduct planned production on a industrial scale. As a method comprising for culturing lichen cells to be extracted and collecting a lichen component from the cells, for example, there is the present inventor's application (Japanese Patent Application No. 58-56689), however, superoxide elimination action is not described.

It is known that active oxygen species (e.g. superoxide, hydroxy radical, singlet oxygen, etc.) act as an important protection factor in a living body. For example, when virus or foreign body invades a living body, phagocytes (e.g. neutrophil, monocyte, macrophage, etc.) is activated to express a dynamic function such as migration ability, phagocytosis and the like, whereby, lysosome enzyme or superoxide is produced and discharged. These are directly or indirectly concerned with fusion and sterilization of ingesta to protect a body from a foreign enemy.

On the other hand, active oxygen species cause various tissue disorder if they are present in an excessive amount in a living body. The amount of superoxide which is considered to be the representative of active oxygen species produced in a body is about 1% or less based on the amount of oxygen absorbed by respiration, and superoxide is gradually eliminated by catalysis of superoxide dismutase (SOD) contained in cells. However, when an oxygen action is deteriorated as is observed in a body of the old, elimination is not completely conducted and, therefore, a concentration of superoxide becomes high, which results in tissue disorder (e.g. articular rheumatism, etc.) as well as cardiac infarction, cerebral hemorrhage, cataract, blotch and ephelis which are caused by superoxide or lipoperoxide produced thereform.

A skin is an organ wherein superoxide is particularly liable to be formed because it is directly subjected to stimulation of environmental factors (e.g. ultraviolet ray, etc.). Therefore, increase of the superoxide concentration and formation of lipoperoxide are liable to be arisen, whereby, disorders (e.g. formation of melanin pigment, blotch, fine wrinkle, etc.) are liable to be arisen.

Superoxide dismutase (SOD) is an enzyme having an ability to eliminate superoxide in a living body, but a half-time in the living body is short (within 5 minutes) and it is inferior in safety.

OBJECTS OF THE INVENTION

One object of the present invention is to provide an extract or active substance having stable superoxide elimination activity in a living body derived form natural lichens or lichen cultures.

Another object of the present invention is to provide a process for producing the same.

Still another object of the present invention is to provide cosmetics containing the extract or active substance having stable superoxide elimination activity.

These objects as well as other objects and advantages of the present invention will become apparent to those skilled in the art from the following description.

SUMMARY OF THE INVENTION

According to the present invention, there is provided a superoxide eliminating agent comprising a component extracted from natural lichens or lichen cultures, and a process for producing the same.

DETAILED EXPLANATION OF THE INVENTION

The lichen cultures used in the present invention can be derived from any lichens which belong to the following families by a normal method. For example, a method disclosed in Japanese Patent Kokai No. 58-56689 can be employed. Examples of lichens include Teloschistaceae, Physciaceae, Buelliaceae, Usneaceae, Anziaceae, Parmeliaceae, Candelariaceae, Lecanoraceae, Pertusariaceae Acarosporaceae, Umbilicariaceae, Cladoniaceae, Baeomycetaceae, Streocaulaceae, Lecideaceae, Gyalectaceae, Asterothyriaceae, Stictaceae, Peltigeraqceae, Pannariaceae, Coccocarpiaceae, Placynthiaceae, Heppiaceae, Collemataceae, Lichnaceae, Graphidaceae, Thelotremataceae, Diploschistaceae, Verrucariaceae, Pyrenulaceae, Strigulaceae, Sphaerophoraceae, Caliciaceae, Cypheliaceae, Lecanactidaceae, Opegraphaceae, Arthopyreniaceae, Arthoniaceae, Dictyonemataceae, Clavariaceae, Agariaceae and the like. Among them, substances having high superoxide elimination activity can be obtained from lichens which belong to the family Graphidaceae, Parmeliaceae, Teloschistaceae and Usneaceae, and they are preferred. The term "lichen culture" used herein means a culture of lichen cells, algae cells or indifferent symbiotic cultured tissue wherein both cells are present.

Among lichens used in the present invention, lichens which belong to Usneaceae, Parmeliaceae, Lecanoraceae, Pertusariaceae, Umbilicariaceae, Cladoniaceae, Lecideaceae, Stereocaulaceae, Teloschistaceae, Peltigeraceae and Graphidaceae are particularly preferred.

A culture medium used in the present invention is not specifically limited. Normally, a culture medium which is used for cultures of lichens, or modified culture medium may be used. The culture medium contains microorganic matters, for example, carbon source, nitrogen source, inorganic ion source, vitamins and the like. Examples of the carbon source include carbohydrates (e.g. sucrose, mannitol, etc.) or derivative thereof. Examples of the nitrogen source include nitrogen-containing compounds such as complicated protein decomposition products (e.g. ammonium ion, nitrate ion, amino acid, peptone, etc.). Examples of the inorganic ion source include inorganic salts (e.g. calcium chloride, magnesium sulfate, etc.) consisting of cations (e.g. potassium ion, calcium ion, mangensium ion, iorn ion, etc.) and anions (e.g. sulfate ion, phosphate ion, chloride ion, etc.). Examples of vitamins include thiamin, pyridoxin, nicotinic acid, inositol and the like. As the microorganic matter, phytohormones such as auxins (e.g. 2,4-dichlorophenoxyacetic acid, naphthalene acetic acid, etc.), cytokinins (e.g. kinetin, benzyl adenin, etc.) and the like may be added. As the culture medium used in the present invention, for example, there are modified culture mediums such as Lillie Burnet's culture medium, Hamada's culture medium, malt yeast extract and the like. These culture mediums are used after pH is adjusted to about 6.

The incubation is normally conducted for 3 weeks to 6 months, using above-mentioned solid or liquid culture medium. The incubation temperature varies depending on a kind of lichen cultures, and the incubation is conducted under a constant temperature at 10° to 30° C., preferably 15° to 20° C.

In order to extract a superoxide elimination active substance from natural lichens or lichen cultures, the resulting lichen cultures or collected natural lichens are directly dipped in a solvent, or dipped in a solvent after they are treated with a drying means (e.g. freeze-drying, etc.). The dipping is conducted at low temperature (0° to 15° C.) for 1 to 24 hours, which is due to stability of the superoxide elimination active substance. The solvent may be water, polar organic solvent and nonpolar organic solvent. In view of extraction efficiency, polar solvents (e.g. alcohol, ketone, ester, etc.) are preferred (particularly acetone).

Then, the dipping solution was filtered off and the solvent of the resulting extrac solution was distilled off to obtain a superoxide elimination active substance.

The dosage of the superoxide elimination active substance may be 0.01 to 0.1 g, preferably 0.08 to 0.1 g a day, but it is not specifically limited.

The superoxide eliminating agent of the present invention can be administered in various forms. In general, it is used in the form of oral preparations or external preparations. Further, it may be formulated in cosmetics. All dosage forms of drugs are known to the art.

The superoxide eliminating agent comprising a component extracted from natural lichens or lichen cultures is extremely stable and it can be employed for drugs for preventing or treating diseases caused by the excessive amount of superoxide (e.g. ischemic cardiac disease, etc.) or cosmetics for preventing oxygen disorder.

The present invention will be further explained in detail in the following examples, but it is not construed to limit to them.

Measurement of Superoxide Elimination Activty

To a 0.1 mM phosphate bubber solution (0.5 ml) containing 0.4 mM xanthine and 0.24 mM nitroblue tetrazolium, a 0.1 mM phosphate buffer solution containing xanthine oxidase (0.049 U/ml) and lichen extract sample (which was prepared by adding an aqueous 1% triton-x solution to 10 mg of extract) (0.05 ml) were added and reacted at 37° C. for 20 minutes. Then, formation of diformazane due to the reaction of superoxide with nitroblue tetrazolium was measured at 560 nm. The degree of decrease of an absorbance to control was defined as superoxide elimination activity.

EXAMPLES 1

80 Kinds of lichen cultures were freeze-dried and aceton (10 ml) was added to the freeze-dried article (200 mg), followed by extraction at 4° C. for twenty-four hours. After filtration, the solvent was distilled off. To the obtained extract (10 mg), a aqueous 11% triton-x solution (1 ml) was added to form a sample to measure superoxide elimination activity. The following numerical value in parenthesis indicates superoxide elimination activity (%).

Among natural lichens, *Usnea diffracta* (65.5%), *Cetraria ornata* (43.1%), *Lecanora decolata* (42.8%), *Ochlorechia yasudae* (54.9%), *Umbilicaria pensylvania* (74.1%), *Cladonia phylfora* (60.1%), *Stereocaulon nigram* (37.9%), *Xantoria fallax* (76.9%), *Lecidea skararis* (37.8%), *Peltigera venosa* (42.7%) and *Graphis scripta* (63.2%) showed superoxide elimination activity which matches or exceeds SOD.

Among lichen cultures, *Cetraria canadiensis* (96.9%), *Cladonia conistea* (90.9%), *Graphis scripta* (87.6%), *Xantoria parientina* (71.0%) and *Usnea filipendula* (92.9%) showed superoxide elimination activity which matches or exceeds SOD. Further, their activity was stable after the sample was stored for a long period of time.

What is claimed is:

1. A method of eliminating superoxide in a living organism in need thereof comprising applying externally to skin a superoxide eliminating agent obtained from natural lichens or lichen cultures by extraction with a polar organic solvent, wherein the superoxide eliminating agent is recovered from the solvent.

2. The method of claim 1, wherein the natural lichens or lichen cultures are dried before contact with the solvent.

3. The method of claim 1, wherein the natural lichens or lichen cultures are freeze-dried before contact with the solvent.

4. The method of claim 1, wherein the process is carried out at a temperature of from about 0° C. to 15° C. for a period sufficient to extract superoxide eliminating agent.

5. The method of claim 1, wherein the natural lichens or lichen cultures are dipped in the polar organic solvent from 1 to 24 hours to obtain an extract.

6. The method of claim 1, wherein the solvent is acetone.

7. The method of claim 1, wherein the natural lichens or lichen cultures are freeze-dried and then dipped into a polar organic solvent at a temperature of from about 0° C. to 15° C. for 1 to 24 hours to obtain an extract.

8. The method of claim 1, wherein the natural lichens belong to the family selected from the group consisting of Usneaceae, Parmeliaceae, Lecanoraceae, Pertusariaceae, Umbilicariaceae Cladoniaceae, Lecideaceae, Stereocaulaceae, Teloschistaceae, Peltigeraceae and Graphidaceae.

9. The method of claim 1, wherein the lichen cultures belong to the family selected from the group consisting of Graphidaceae, Parmeliaceae, Teloschistaceae and Usneaceae.

10. A method of eliminating superoxide in a living organism in need thereof comprising administering orally a superoxide eliminating agent obtained from natural lichens or lichen cultures by extraction with a polar organic solvent, wherein the superoxide eliminating agent is recovered from the solvent.

11. The method of claim 10, wherein the natural lichens or lichen cultures are dried before contact with the solvent.

12. The method of claim 10, wherein the natural lichens or lichen cultures are freeze-dried before contact with the solvent.

13. The method of claim 10, wherein the process is carried out at a temperature of from about 0° C. to 15° C. for a period sufficient to extract superoxide eliminating agent.

14. The method of claim 10, wherein the natural lichens or lichen cultures are dipped into the polar organic solvent from 1 to 24 hours to obtain an extract.

15. The method of claim 10, wherein the solvent is acetone.

16. The method of claim 10, wherein the natural lichens or lichen cultures are freeze-dried and then dipped into a polar organic solvent at a temperature of from about 0° C. to 15° C. for 1 to 24 hours to obtain an extract.

17. The method of claim 10, wherein the natural lichens belong to the family selected from the group consisting of Usneaceae, Parmeliaceae, Lecanoraceae, Pertusariaceae, Umbilicariaceae Cladoniaceae, Lecideaceae, Stereocaulaceae, Teloschistaceae, Peltigeraceae and Graphidaceae.

18. The method of claim 10, wherein the lichen cultures belong to the family selected from the group consisting of Graphidaceae, Parmeliaceae, Teloschistaceae and Usneaceae.

19. The method of claim 10, wherein the superoxide eliminating agent is administered in an amount of from 0.01 to 0.1 grams per day.

* * * * *

UNITED STATES PATENT AND TRADEMARK OFFICE
CERTIFICATE OF CORRECTION

PATENT NO. : 5,447,721

DATED : September 5, 1995

INVENTOR(S) : Yasutaka Miura, et al

It is certified that error appears in the above-indentified patent and that said Letters Patent is hereby corrected as shown below:

On the title page, item [75], change "Yasuhiro Knoshita" to --Yasuhiro Kinoshita--.

Signed and Sealed this

Fifth Day of March, 1996

*Attest:*

BRUCE LEHMAN

*Attesting Officer*     Commissioner of Patents and Trademarks